(12) United States Patent
Rowell

(10) Patent No.: US 7,781,225 B2
(45) Date of Patent: Aug. 24, 2010

(54) SURFACE LAYER AFFINITY-CHROMATOGRAPHY

(75) Inventor: Frederick John Rowell, Durham (GB)

(73) Assignee: University of Sunderland, Sunderland (GB)

( * ) Notice: Subject to any disclaimer, the term of this patent is extended or adjusted under 35 U.S.C. 154(b) by 0 days.

(21) Appl. No.: 10/542,883

(22) PCT Filed: Jan. 20, 2004

(86) PCT No.: PCT/GB2004/000200
§ 371 (c)(1), (2), (4) Date: Dec. 27, 2005

(87) PCT Pub. No.: WO2004/065962
PCT Pub. Date: Aug. 5, 2004

(65) Prior Publication Data
US 2006/0172434 A1 Aug. 3, 2006

(30) Foreign Application Priority Data
Jan. 20, 2003 (GB) .................................. 0301225.9

(51) Int. Cl.
*G01N 21/00* (2006.01)
*G01N 15/06* (2006.01)
*G01N 30/02* (2006.01)
*G01N 33/53* (2006.01)
*G01N 21/77* (2006.01)
*G01N 33/558* (2006.01)
*G01N 33/543* (2006.01)
*G01N 33/544* (2006.01)
*C12Q 1/00* (2006.01)
*C12M 1/34* (2006.01)
*C12M 3/00* (2006.01)

(52) U.S. Cl. .................... 436/518; 422/55; 422/56; 422/57; 422/68.1; 422/70; 435/4; 435/7.1; 435/287.1; 435/287.2; 435/287.7; 436/514; 436/528; 436/164; 436/169

(58) Field of Classification Search ............... 422/55, 422/56, 57, 68.1, 70; 435/4, 7.1, 287.1, 287.2, 435/287.7; 436/514, 518, 528, 164, 169
See application file for complete search history.

(56) References Cited

U.S. PATENT DOCUMENTS 4,235,601 A * 11/1980 Deutsch et al. ............. 436/514

(Continued)

FOREIGN PATENT DOCUMENTS

EP 0889327 7/1999

(Continued)

OTHER PUBLICATIONS

International Search Report mailed Aug. 5, 2004.

(Continued)

*Primary Examiner*—Gailene R Gabel
*Assistant Examiner*—Jacqueline Diramio
(74) *Attorney, Agent, or Firm*—Hunton & Williams LLP

(57) ABSTRACT

There is described an affinity-chromatography assay system comprising with an immobilized component containing a bio-reagent and a flowable component containing a complimentary bio-reagent characterized in that the immobilized component is supported on a dip strip or planar surface and the flowable component is adapted to flow down the dip strip of high density. There is also described a method of conducting an affinity-chromatography assay which comprises the use of such an assay system.

39 Claims, 1 Drawing Sheet

U.S. PATENT DOCUMENTS

Figure 1:
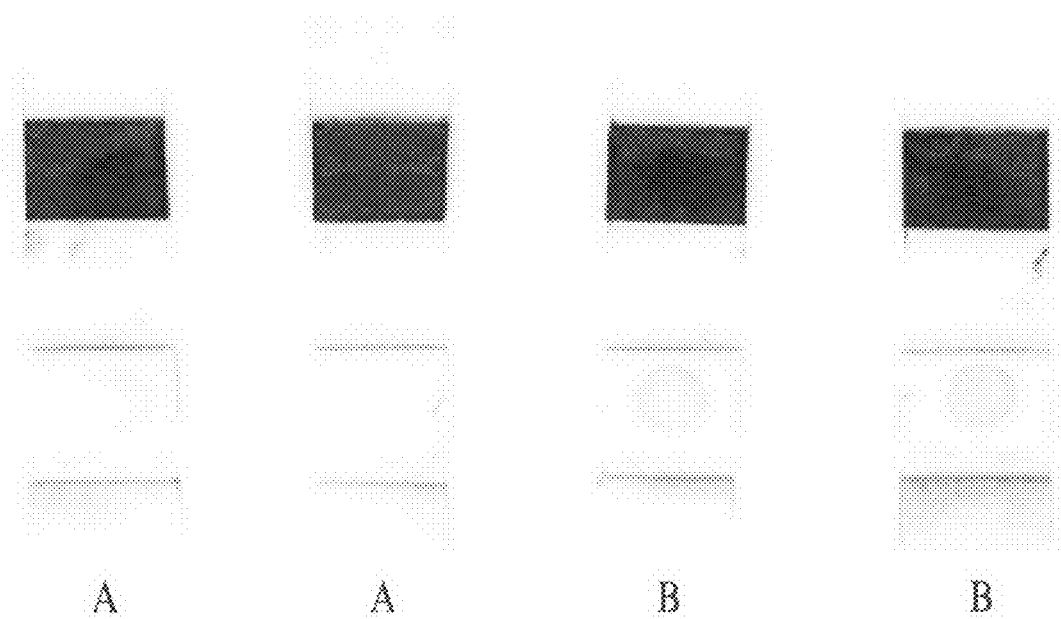

| | | | | |
|---|---|---|---|---|
| 4,943,522 | A | * | 7/1990 | Eisinger et al. ............ 435/7.25 |
| 5,013,669 | A | | 5/1991 | Peters, Jr. |
| 5,602,040 | A | * | 2/1997 | May et al. ................... 436/514 |
| 5,731,157 | A | * | 3/1998 | Miller et al. ................. 435/7.4 |
| 5,773,234 | A | | 6/1998 | Pronovost et al. |
| 6,287,875 | B1 | * | 9/2001 | Geisberg .................... 436/518 |
| 6,534,320 | B2 | * | 3/2003 | Ching et al. ................ 436/518 |
| 6,723,500 | B2 | * | 4/2004 | Yu ................................ 435/4 |
| 7,329,738 | B1 | * | 2/2008 | Lee et al. ................. 530/391.1 |
| 2002/0001818 | A1 | * | 1/2002 | Brock ......................... 435/7.1 |
| 2002/0045195 | A1 | * | 4/2002 | Hubscher et al. ............ 436/514 |
| 2003/0207442 | A1 | * | 11/2003 | Markovsky et al. ....... 435/287.2 |

FOREIGN PATENT DOCUMENTS

| | | |
|---|---|---|
| EP | 0 982 590 | 3/2000 |
| EP | 1 143 247 | 10/2001 |
| JP | 11-64336 | 3/1999 |
| JP | 2000-19178 | 1/2000 |

OTHER PUBLICATIONS

Mark, et al., "A New Personal Sampler for Airborne Total Dust in Workplaces," Ann. Occup. Hyg., vol. 30, No. 1, pp. 89-102, 1986.

Vincent, "Measurement of Fine Aerosols in Workplaces, : A Review," Analyst, vol. 119, pp. 19-25, Jan. 1994.

Vincent, "Measurement of Coarse Aerosols in Workplaces, : A Review," Analyst, vol. 119, pp. 13-18, Jan. 1994.

Vincent, et al., "Entry Characteristics of Practical Workplace Aerosol Samplers in Relation to the ISO Recommendations," Ann. Occup. Hyg., vol. 34, No. 3, pp. 249-262, Jan. 1990.

Dunn, et al., "The Use of $N,N$-Dimethylcasein in the Determination of Proteolytic Enzymes in Washing Products and Airborne Dust Samples," Analyst, vol. 96, pp. 159-163, Feb. 1971.

Flindt, "Pulmonary Disease Due to Inhalation of Derivatives of *Bacillus subtilis* Containing Proteolytic Enzyme," The Lancet, pp. 1177-1181, Jun. 1969.

Hamilton, et al., "Ara12 subtilisin-like protease from *Arabidopsis thaliana*: purification, substrate specificity and tissue localization," Biochem. J., 370, pp. 57-67, 2003.

COSHH Regulations 1999 proposals for maximum exposure levels and occupational exposure standards (consultative document) (1999).

http://www.lsbu.ac.uk/biology/enztech/detergent.html (2004); [Retrieved on Apr. 21, 2008].

COSHH Regulations 2002 Proposals for new maximum exposure limit (consultative document) (2002).

Health and safety commission, Advisory committee on toxic substances. Substisilins-proposal for a MEL paper No. ACTS/08/2003.

L.A. Wallace and W.R. Ott, *J. of the Air Pollution Control Assoc.*, vol. 30, pp. 601-610, 1986.

* cited by examiner

SURFACE LAYER AFFINITY-CHROMATOGRAPHY

Immuno-chromatography is currently performed in two major formats. The first is performed within gels when development is achieved by passive diffusion or is electrochemically induced, and the second is performed in flow. In the former using gels, radial immunodiffusion is the most commonly used system with a preformed gel often located within a circular plate in which a central well is present in the gel together with additional wells located around the edge of the gel. Antiserum or antigen is placed in the central well and antigen or antiserum is placed in the peripheral wells. Passive diffusion occurs within the gel and white bands of immuno-complex are seen within the gel due to antibody-antigen complex formation. In the electrochemical system antibody/antigen migration within the gel is induced using an electric current.

In the flow-based systems the antibody or antigen is often immobilised within a cartridge which is paced with a liquid flow system such as a flow injection analysis system. The complementary antigen or antibody is injected and flows through the cartridge where specific interactions take place. Often the component that is injected carries a label that can be detected downstream, thereby producing a signal. Alternatively flow occurs over a planar surface as in lateral flow diffusion immunoassay systems where flow is induced by membrane wetting/capillarity.

In the new format the equivalent immunoreactions take place in flow between an immobilised component and one in solution as above but this now occurs on the surface of a dip strip residing within a buffer solution. In this case flow across the surface of the strip occurs due to the higher density of a solution containing one of the immunoreagents that is initially present at the top of the strip that is itself standing in the buffer solution. Since the strip is nearly upright this denser solution slowly rolls down the surface of the strip presenting the reagent in the flowing phase to the immobilised reagent on the surface of the dip strip.

Thus according to the invention we provide an affinity-chromatography assay system comprising with an immobilised component containing a bio-reagent and a flowable component containing a complimentary bio-reagent characterised in that the immobilised component is supported on a dip strip or other planar surface and the flowable component of high density is adapted to flow down the dip strip.

In order for this phenomenon to work certain criteria must be met. Firstly the denser solution must be retained in a discrete volume as it passes as a layer over the surface rather than rapidly diffusing into the bulk of the buffer solution. Secondly the dip strip must possess certain properties that result in attraction of the rolling surface layer again leading to retention of the integrity of this mobile phase. To achieve the first criterion we have carefully chosen the constituents of the rolling phase to include a polymeric agent such as a protein and/or a polysaccharide, a detergent and a buffer of optimal pH, and for the second we use a membrane that is both hydrophobic and wettable.

The system can be used as an immuno-chromatography system and assays performed in either competitive or non-competitive immunoassay formats. In the former the immobilised spot is either antibody or antigen. For immobilised antibody, a labelled antigen is deposited in a band above the spot in a cellulose square. A drop of sample containing the antigen is added to this square and after a suitable interval (1-10 min) the whole strip is immersed in a buffer solution. The dense mixture of labelled and unlabelled antigen flows over the spot of antibody and competition for binding takes place. If the antigen is immobilised at the spot, a labelled antibody replaces the labelled antigen in the cellulose square and the assay proceeds as before.

The system can also be performed in a non-competitive immunoassay format when a spot of capture antibody is immobilised on the strip. Labelled antibody is deposited on the cellulose square above the first spot. The strip is placed in the sample solution containing the antigen so that the upper square is immersed. Incubation now takes place during which antigen in the solution is captured by immobilised antibody on the spot. At the same time the labelled antibody is reconstituted in a dense solution that flows over the spot after about 5-10 minutes following insertion of the strip into the sample solution. This time lag enables antigen molecules to be captured on the spot prior to arrival of the surface layer containing the labelled antibody. This second antibody labels the captured antigen on the spot's surface.

In addition any label can be used. If a fluorescent or coloured label is used with the antibody or antigen, then a fluorescent or coloured spot will result following the first incubation, making the assay a single step system.

If an enzyme label is used then a modified sequence of steps can be used in the non-competitive assay. In this, enzyme-labelled antibody is now added to the cellulose square attached to the bottom of the strip beneath the spot of immobilised capture antibody. A second cellulose square is also attached as before above this spot but this contains a dried solution of substrate for the enzyme plus a biopolymer such as dextran. The strip is placed in a limited volume of sample as before so as not to wet the upper cellulose square. The dense reconstituted solution of labelled antibody flows to the bottom of the container and stays there as a separate layer. At the same time antigen in solution is captured by the antibody on the spot. At the end of this incubation step (5-10 minutes) the solution is stirred using the dip strip. This causes the labelled antibody to be homogeneously distributed within the solution and the antibody can now bind to the captured antigen on the spot. Finally the volume in the container is increased to wet the upper cellulose square. The substrate is now reconstituted as a dense solution that flows over the spot when substrate to product conversion takes place resulting in a coloured spot.

According to a further aspect of the invention we provide a method of conducting immuno-chromatography assays which comprise the use of an assay system as hereinbefore described.

This new surface layer chromatography phenomenon could, in theory, also be used as a generic chromatographic method for separation of analyte mixtures if the components have different binding affinities for the surface. For example, it is well known that biological polymers such as proteins and DNA/RNA bind to cellulose nitrate as this is used in DNA- and protein-blotting following electrophoresis. We have also observed that for antibodies the rate of binding to this surface is pH sensitive [1]. Hence it should be possible to introduce a mixture of biological polymers onto a cellulose strip above a cellulose nitrate square. The pH and density of the buffer used would be such that surface layer chromatography will ensue when the strip is immersed into a second buffer solution chosen to optimise the binding of the biopolymers to the surface. Under these conditions, different binding interactions will take place between the bio-molecules and the surface as the mobile phase layer rolls over the surface. This should lead to separation of the components during this development phase. The strip would then be removed and the membrane treated to visualise, using established methods, the now immobilised components of the mixture.

The invention will now be illustrated with reference to the accompanying example.

EXAMPLE 1

In an example of this new immunochromatographic system that we term Surface Layer Immuno-Chromatography (SLIC), a small square of cellulose nitrate membrane is pretreated via established methods with a specific antibody to an antigen such as savinase, to produce a spot of immobilised reagent. This square is stuck on the surface of a plastic strip pre-coated with one sticky surface. Above this is stuck a second strip of cellulose impregnated with a dried solution of the same antibody labelled with the reporter enzyme alkaline phosphatase, together with bovine serum albumin (BSA) and Tween 20. The solution used for this deposition is Tris (pH 9.3) and a volume of 10 µl is used. The composition of this solution is 0.1% w/v BSA, 0.1% w/v Tween 20, enzyme-labelled antibody diluted 1:1000 in Tris buffer (0.1M). The reagents in this format when stored at room temperature in a desiccator are stable on the strip for at least 14 days.

To perform the assay, a solution of savinase (0.3 ml) in Tris buffer is placed in a test tube such as a conventional 96 well microtitre plate. The dip strip is now inserted into the well when both squares are covered by the sample. On wetting, the reagents within the square of cellulose pass into solution. Due to its higher density this solution now flows as a layer down the surface of the strip and eventually passes over the lower square containing the spot of immobilised antibody. In the time interval between immersion of the strip and arrival of the flowing phase, savinase molecules in the bulk solution will have been captured by the immobilised antibodies on the lower spot. On arrival of the flowing phase, labelled antibody will bind to the captured antigen molecules as in a conventional sandwich-type ELISA, as the solution flows over the spot. This first incubation period is typically 15 minutes.

The strip is removed from the well and placed in wells containing the commonly used substrate mixture for alkaline phosphatase, bromochloroindolyl phosphate (BCIP) and nitroblue tetrazolium salt (NBT). A purple/blue colour develops after 1 minute's incubation, the intensity of which is directly proportional to the amount of savinase captured on the spot during the first incubation step, and hence the concentration of savinase in the sample. The top square is also coloured purple/blue. A scan of the resulting strips is shown for this analyte. It should be noted that we use 12 such strips in a comb-like format as this enables analysis of up to 96 samples/standards (8×12) to be performed with a single microtitre plate. It will be noted that visual discrimination between the zero and the 5 ng/ml standard is clearly seen.

EXAMPLE 2

As in example 1, a small square of cellulose nitrate membrane with a spot of specific antibody is attached to the surface of a plastic strip. Below this a second strip of cellulose (cut as 0.4×0.6 cm squares from fast hardened filter paper) is placed. This square is impregnated with a 5 µl of a diluted solution of the same antibody labelled with the reporter enzyme alkaline phosphatase, in a solution of blue dextran, (3% w/v), dextran (25 w/v), all in Tris buffer with azide, pH 9.3 (containing 0.1% Tween 20 and 0.15 (w/v) bovine serum albumin). The applied solution is allowed to dry at ambient temperature for 30 minutes. A third square of fast hardened filter paper is stuck above the first square and is impregnated with the substrate for alkaline phosphatase. This is prepared by addition of 15 µl of a mixture of 1% (w/v) blue dextran, 1% (w/v) dextran and BCIP-NBT stock solution. It is allowed to dry for 60 minutes at ambient temperature at which point the square is stuck to the dip strip.

The pre-prepared dip strips are then added to microcuvettes containing 0.6 ml of standards or samples. After 10 minutes a blue layer of solution is observed at the base of the cuvette. The strips are used to stir the contents of the cuvettes. This produces a uniform blue coloration throughout the solution. Incubate for a further 5 minutes then add 500 µl of substrate buffer solution to now cover the top square on the dip strip. Incubate for a final 10 minutes, then remove the strips and wash with water.

When rabbit anti-savinase antibodies are used as the capture and capping antibodies in the presence of savinase standards, the following strips are observed when the above protocol is followed.

The resulting dip strips are illustrated in FIG. 1, in which:
A=zero standards, B=10 ng/ml standards of savinase

The invention claimed is:

1. An affinity-chromatography strip having a planar surface and a longitudinal axis, said strip comprising:
   (a) a first location having a first movably immobilized flowable component comprising a first bio-reagent and a biopolymer;
   (b) a second location having a second immobilized component comprising a second bio-reagent; and
   (c) optionally a third location having a third immobilized component comprising a third bio-reagent;
   wherein said first and second locations are spaced at a first distance along the longitudinal axis and said third location, when present, is spaced at a second distance along said longitudinal axis from said second location; and
   wherein the flowable component, when entirely immersed in a buffer solution optionally comprising a fourth bio-reagent, forms a discrete volume at the first location that:
      (i) comprises said first bio-reagent;
      (ii) is denser than the buffer solution;
      (iii) does not diffuse rapidly into the buffer solution; and
      (iv) slowly rolls, under the influence of gravity, over said planar surface along said longitudinal axis in the direction of said second location.

2. An affinity-chromatography strip according to claim 1, wherein the first bio-reagent is an antigen or an antibody.

3. An affinity-chromatography strip according to claim 1, wherein the flowable component further comprises a detergent and a buffer of optimal pH.

4. An affinity-chromatography strip according to claim 1, wherein the first movably immobilized flowable component possesses properties that result in attraction of the flowable component.

5. An affinity-chromatography strip according to claim 1, wherein the first bio-reagent comprises a labelled antigen and the second bio-reagent comprises an unlabelled antibody.

6. An affinity-chromatography strip according to claim 5, wherein the labeled antigen comprises a fluorescent or colored label.

7. An affinity-chromatography strip according to claim 1, wherein said first movably immobilized flowable component, or said second, or third immobilized components comprise a membrane.

8. An affinity-chromatography strip according to claim 7, wherein the membrane is hydrophobic and wettable.

9. An affinity-chromatography strip according to claim 1, wherein the second bio-reagent is an antigen or an antibody.

10. An affinity-chromatography strip according to claim 1, wherein the first bio-reagent comprises a labelled antibody and the second bio-reagent comprises an unlabelled antigen.

11. An affinity-chromatography strip according to claim 10, wherein the labeled antibody comprises a fluorescent or colored label.

12. An affinity-chromatography strip according to claim 1, wherein the second bio-reagent comprises a first antibody and the third bio-reagent comprises a second antibody, wherein the first antibody and the second antibody specifically bind to a common antigen.

13. An affinity-chromatography strip according to claim 12, wherein the third bio-reagent is a labelled antibody.

14. An affinity-chromatography strip according to claim 13, wherein the labelled antibody is an enzyme labelled antibody.

15. An affinity-chromatography strip according to claim 14, wherein the first bio-reagent comprises a substrate for said enzyme.

16. An affinity-chromatography strip according to claim 15, wherein the substrate comprises bromochloro indolyl phosphate-nitroblue tetrazolin salt (BCIP-NBT).

17. An affinity-chromatography strip according to claim 13, wherein the label comprises alkaline phosphatase.

18. An affinity-chromatography strip according to claim 12, wherein the first antibody and the second antibody are specific to savinase.

19. An affinity-chromatography strip according to claim 12, wherein the biopolymer comprises dextran, dextran blue, or combinations thereof.

20. An affinity-chromatography strip according to claim 12, wherein the first, second, or third immobilized components comprise a nitrocellulose membrane.

21. An affinity-chromatography strip according to claim 5, wherein the fourth bio-reagent comprises a non-labelled antigen.

22. An affinity-chromatography strip according to claim 1, wherein the first bio-reagent comprises a labelled antibody and the second bio-reagent comprises an unlabelled antibody.

23. An affinity-chromatography strip according to claim 22, wherein the labeled antibody comprises a fluorescent or colored label.

24. A kit comprising the affinity-chromatography strip according to claim 1.

25. The kit of claim 24, wherein the first bio-reagent comprises a labelled antigen and the second bio-reagent comprises an unlabelled antibody.

26. The kit of claim 24, wherein the first bio-reagent comprises a labelled antibody and the second bio-reagent comprises an unlabelled antigen.

27. The kit of claim 25, wherein the labeled antibody comprises a fluorescent or colored label.

28. The kit of claim 24, wherein the first bio-reagent comprises a labelled antibody and the second bio-reagent comprises an unlabelled antibody.

29. The kit of claim 28, wherein the labeled antibody comprises a fluorescent or colored label.

30. The kit of claim 28, wherein the labeled antibody comprises an enzyme label.

31. The kit of claim 24, wherein the second bio-reagent comprises a first antibody and the third bio-reagent comprises a second antibody, wherein the first antibody and the second antibody specifically bind to a common antigen.

32. The kit of claim 31, wherein the third bio-reagent is a labelled antibody.

33. The kit of claim 32, wherein the labelled antibody is an enzyme labelled antibody.

34. The kit of claim 33, wherein the first bio-reagent comprises a substrate for said enzyme.

35. The kit of claim 34, wherein the substrate comprises BCIP-NBT.

36. The kit of claim 32, wherein the label comprises alkaline phosphatase.

37. The kit of claim 31, wherein the first antibody and the second antibody are specific to savinase.

38. The kit of claim 24, wherein the biopolymer comprises dextran, dextran blue, or combinations thereof.

39. The kit of claim 28, wherein the labeled antibody comprises a fluorescent or colored label.

* * * * *